(12) United States Patent
Yu et al.

(10) Patent No.: US 6,528,084 B2
(45) Date of Patent: Mar. 4, 2003

(54) COMPOSITION AND METHOD

(75) Inventors: Shiguang Yu, Topeka, KS (US); Claudia Kirk, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 0 days.

(21) Appl. No.: 09/745,130

(22) Filed: Dec. 21, 2000

(65) Prior Publication Data

US 2002/0114841 A1 Aug. 22, 2002

(51) Int. Cl.⁷ .................. A61K 47/00; A23L 1/05; A23L 1/06; A23K 1/18
(52) U.S. Cl. ............. 424/439; 424/400; 424/438; 424/442; 426/573; 426/576; 426/578; 426/805
(58) Field of Search ................. 424/400, 438, 424/439, 442

(56) References Cited

U.S. PATENT DOCUMENTS

| | | |
|---|---|---|
| 5,217,740 A | 6/1993 | Lanter ................. 426/573 |
| 5,279,838 A | 1/1994 | McNeff |
| 5,799,609 A | 9/1998 | Evans et al. |
| 6,171,632 B1 | 1/2001 | Lanter et al. ........... 426/573 |

OTHER PUBLICATIONS

Patent Abstracts of Japan, vol. 011, No. 139 (C–420), May 7, 1987 (May 7,1987) and JP 61 277630 A (Morinaga Milk Ind. Co. Ltd.; others: 01), Dec. 8, 1986 (Dec. 8, 1986) abstract.

Patent Abstracts of Japan, vol. 018, No. 316 (C–1213), Jun. 16, 1994 (Jun. 16, 1994) and JP 06 070695 A (Nisshin Flour Milling Co., Ltd.), Mar. 15, 1994 (Mar. 15, 1994) Abstract.

*Primary Examiner*—Thurman K. Page
*Assistant Examiner*—Charesse Evans
(74) *Attorney, Agent, or Firm*—Martin B. Barancik

(57) ABSTRACT

An aqueous gel suitable for ingestion by a cat or dog comprising,
  a. an effective amount of a gelling agent,
  b. an effective amount of a cat or dog palatability enhancing agent, and
  c. at least about 85 wt. % water.

6 Claims, No Drawings

COMPOSITION AND METHOD

BACKGROUND OF THE INVENTION

Dogs and cats suffer from numerous disorders of the lower urinary tract. Among these are idiopathic urinary tract disease, crystalluria, bacterial cystitis, urolithiasis, idiopathic obstruction, urethal plugs, and the like. Lower Urinary Tract Disease (LUTD) is a disorder common to cats. Urolithiasis, i.e., stone formation in the urinary tract, is a condition commonly found in both dogs and cats. Although the etiology of these disorders are not completely clear, at least some of the factors associated with these disorders appear to be concentrated urine (i.e., high urine specific gravity) or high mineral supersaturation of urine. Lowering mineral concentrations in the urine by increasing urine production through increased water consumption can reduce the risk of urinary crystal or stone formation, assist in dissolving certain types of formed urinary tract stones, as well as reduce the occurrence of feline LUTD. In addition, increased urine volume initiates more frequent voiding. Frequent voiding further reduces risk of urinary tract infection, crystalluria and urolithiasis.

We have found that a high moisture palatable gel can significantly increase total water intake and urine production in a companion pet such as a dog or cat. Thus, it can be used to prevent and/or treat lower urinary tract disorder(s) including: crystalluria, urolithiasis, cystitis, idiopathic obstruction, urethal plugs, and feline LUTD in a companion pet such as a dog or cat. In addition, it can be an aide to increasing total water intake and improving hydration in conditions such as diabetes, renal disease, pregnancy, lactation, etc.

SUMMARY OF THE INVENTION

In accordance with the invention there is a gel suitable for ingestion by a dog or cat which comprises,
  a. an effective amount of a gelling agent,
  b. an effective amount of a dog or cat palatability enhancing agent, and
  c. at least about 85 wt. % water.

A further aspect of the invention is wherein the gel is provided to the cat or dog in conjunction with a diet meeting the nutritional needs of the dog or cat.

A still further aspect of the invention is providing the gel to a dog or cat for the purpose of at least assisting in preventing lower urinary tract disorder(s) including crystalluria, urolithiasis, cystitis, LUTD, idiopathic obstruction, urethal plugs, and the like, in said dog or cat. This is particularly useful in dogs or cats at risk for lower urinary tract disorder(s); that is, seem to have a tendency to develop those diseases.

Another aspect of the invention is a method of treating a dog or cat with lower urinary tract disorder which comprises providing a gel of the invention to a dog or cat having such disorders.

DETAILED DESCRIPTION OF THE INVENTION

The usage of the gelled water brings about a much higher total water intake for dogs and cats, lower urinary specific gravity, and a correspondingly higher urine output for them compared to without the gel. Not only is the gelled water very effective in increasing total water intake and urine output but it results in more sightly surroundings since there is no water bowl and splatter, if desired. Additionally, it provides an efficient way of providing water to the pet while traveling or away from its usual settled surroundings. Furthermore, it provides pet owners with a treat of very low energy content. This is particularly useful for pet such as cats and dogs with problems of overweight or obese or other overweight-concerning conditions such as arthritis, diabetes, hypertension, and cardiovascular diseases. In addition, a highly palatable water treat will help improve water balance in animals having higher protein diets and/or having increased water needs, such as diabetes, lactation, exercise, and growth.

The gelling agent employed is any gelling agent that provides a gel with at least 85 wt % water and is acceptable to a dog or cat when orally delivered. Examples of gelling agents that can be employed include gelatin, carrageenan, agar, alginates, pectins, xanthans, guars, gum arabic, gum karaya, gum tragacanth, tara gum, gellan gum, pullulan, curdlan, microcrystalline cellulose (MCC), carboxymethylcellulose (CMC), methylcellulose (MC), hydroxypropyl methylcellulose (HPMC), chitosan, gum ghatti, locust bean, konjac flour, starch and the like.

Generally, a palatability enhancer (flavorant) is employed as well in order to overall enhance the palatability and overcome any negative flavor effects the gelling agent may have to the cat or dog. There are numerous such materials available include animal digest, animal hydrolysates, animal internal organs (such as liver, lungs, and heart), meats (such as beef, lamb, pork, chicken, and turkey), sea foods (such as fish, crab, shrimp), dairy products (such as milk and cheese), yeast, peptides, amino acids, nucleotides, fat, oil, artificial meat and/or sea food flavors, maillard reactants, sugars, plant extracts, and other aromas nature and/or artificial that are attractive to cats or dogs.

The quantity of gelling agent employed is the amount sufficient to bring about a gel that maintains its shape so as to provide an object which is readily eaten by a cat or dog. By maintaining its shape, means an integral structure that can wobble such as "jello" but still maintains its integrity and does not become liquid or flow. Generally, from about 0.05 to about 2 wt. % of the gelling agent as wt. % of the gel, desirably about 0.2 to about 1.5 wt. % can be employed.

The amount of the palatability enhancer is sufficient to bring about a palatability enhancement. This is generally between about 0.1 and 3 wt. % desirably a minimum wt. % of about 0.3 or 0.5 wt. % of the gel.

The amount of water in the gel is generally at least about 85 wt. %, desirably at least about 90 or 95 wt. % or higher.

Other components can be in the gel as well, for example nutrients such as vitamins and minerals used as supplements, preservatives, colorant(s), as well as active agents including antibacterial agent(s), anti-inflammatory agent(s), antiparasitic(s), antioxidant(s), herbal and/or botanical extracts and the like, all in effective quantities. Thus, the gel can function as a delivery system for supplements as well as active ingredients.

The gels of the invention are readily prepared by standard methods. For example, mixing all the components into a container and stirring under conventional or elevated temperatures whenever appropriate, then filling a final shaped container (gel shape) and letting the gel set. More specifically, the following components are used.

TABLE 1

| Component | % |
|---|---|
| Water | 95.48 |
| Kappa carrageenan | 1.5 |
| Chicken hydrolysate | 2.0 |
| Brewer yeast | 0.5 |
| Salt | 0.3 |
| Potassium sorbate | 0.2 |
| FD & C Red No. 40 | 0.02 |
| Total | 100.00 |

Processing Steps
1. Mix the ingredients in a heating container
2. Heat the mixture to 160° F. while stirring
3. Keep the mixture at 160° F. for 15 minutes
4. Fill desired shaped mold with the mixture
5. Let the gel cool and set about 2 hours Below are examples of the invention.

Overall, dogs and cats can experience significant increases in total water intake and urine production as well as a significant decrease in urine specific gravity when utilizing the gel of this invention with a diet meeting nutritional requirements. Utilizing a canned diet, the dog or cat can experience a total water intake increase of at least about 20, desirably at least about 70 or 80%, and a urine production increase of at least about 20, desirably at least about 90 or 100 wt. %. Urine specific gravity can decrease by at least about 20, 30 or desirably at least about 40%. Utilizing a dry diet, the cat or dog can experience a total water intake increase of at least about 15, 20 desirably at least about 25% and a urine production increase of at least about 20, or desirably at least about 30 or 40 wt. %. Urine specific gravity can decrease by at least about 10, 15 or desirably at least about 20%.

Example 1

A crossover study design was used and the study period was eight weeks. Eight adult cats were given deionized water ad libitum and either a canned or dry cat food that was complete and balanced in nutrition. In addition to the food, the gel was provided to the cats in the test group while cats in control group received no gel. At the completion of the study, all cats received all diet and gel combinations. The treatment assignments are described below.

Eight cats were divided into four groups of two each. For the first week, two groups of cats were given canned food and two groups of cats were given dry food. In the second week, the same diets were maintained for each group. However, gel provided to one group of two cats having canned food and one group of two cats having dry food (test group). This was provided for one hour twice a day (08:30 a.m.–09:30 a.m. and 01:00 p.m.–02:00 p.m.). The other groups did not receive the gel (control). In the third week, the same diet was maintained but with no gel. In the fourth week, the control group and test groups were reversed. The control group from week two was now given the gel while the test group from week two was not given the gel. In the fifth week, no gel was given but the two groups of cats that had been on dry diet were now given canned and the two groups that had been on canned were now given dry food. In the sixth week, one group in each diet was given the gel while the other was not. In the seventh week, no gel was provided. In the eighth week, the group that did not have the gel in the sixth week was provided with the gel and the gel was withheld from the group which received the gel in the sixth week.

In this manner, each group of two cats had received the dry diet and the canned diet as well as receiving the gel or not receiving the gel.

During this study period, the intake of water from all sources (gel, water and food), output of urine, and urine specific gravity were measured for each cat. Other parameters measured in the study include weekly body weight, daily food intake, urine pH, and stool quality.

With respect to cats having the canned diet, the average total water intake increased by 70%; urine production increased by 89 wt. %; and urine specific gravity decreased by 35% when the gel was available compared to not having the gel available. All these changes are statistically significant ($p<0.01$).

With respect to cats having the dry diet, the total water intake increased by 20%; urine production increased by 32 wt. %; and urine specific gravity decreased by 16% for cats receiving the gel. All these changes are statistically significant ($p<0.01$).

The other parameters measured, i.e., body weight, food intake, urine pH, and stool quality, were not affected by the gel.

What is claimed is:

1. An aqueous gel suitable for ingestion by a cat or dog consisting essentially of,
    (a) an effective amount of a gelling agent,
    (b) an effective amount of a cat or dog palatability enhancing agent, and
    (c) at least about 85 wt. % water.
2. The aqueous gel of claim 1 wherein the gelling agent is kappa carrageenan.
3. The aqueous gel of claim 1 wherein there is at least about 95 wt. % water.
4. A diet composition meeting the nutritional requirement of a cat or dog in association with an aqueous gel of claim 1.
5. The diet of claim 4 wherein the gelling agent is kappa carrageenan.
6. The diet of claim 4 wherein there is at least about 95 wt. % water.

* * * * *